(12) United States Patent
Muhanna et al.

(10) Patent No.: US 6,716,163 B2
(45) Date of Patent: Apr. 6, 2004

(54) SURGICAL INSTRUMENT HOLDER

(75) Inventors: Nabil L. Muhanna, 2128 Valley Rd., Gainesville, GA (US) 30501; David L. Schalliol, Oakwood, GA (US)

(73) Assignee: Nabil L. Muhanna, Gainesville, GA (US)

( * ) Notice: Subject to any disclaimer, the term of this patent is extended or adjusted under 35 U.S.C. 154(b) by 0 days.

(21) Appl. No.: 09/989,174

(22) Filed: Nov. 21, 2001

(65) Prior Publication Data

US 2002/0058860 A1 May 16, 2002

Related U.S. Application Data (60) Provisional application No. 60/252,279, filed on Nov. 21, 2000.

(51) Int. Cl.[7] ................................................. A61B 1/32
(52) U.S. Cl. ........................................ 600/206; 600/229
(58) Field of Search ..................... 606/130; 600/206, 600/215, 227, 228, 229; 248/276.1, 288.51

(56) References Cited

U.S. PATENT DOCUMENTS

| | | |
|---|---|---|
| 5,104,103 A | 4/1992 | Auchinleck et al. ........... 269/74 |
| 5,201,325 A | 4/1993 | McEwen et al. ............. 428/779 |
| 5,269,305 A | 12/1993 | Corol ....................... 128/653.1 |
| 5,271,384 A | 12/1993 | McEwen et al. ............... 128/20 |
| 5,447,149 A * | 9/1995 | Kikawada et al. ........... 600/229 |
| 5,624,381 A * | 4/1997 | Kieturakis ................... 600/206 |
| 5,776,144 A | 7/1998 | Leysieffer et al. ........... 606/130 |
| 5,891,157 A | 4/1999 | Day et al. .................... 606/600 |
| 5,899,425 A * | 5/1999 | Corey, Jr. et al. ......... 248/276.1 |
| 6,102,853 A * | 8/2000 | Scirica et al. ................ 600/229 |

FOREIGN PATENT DOCUMENTS

EP           0167345       *   8/1986

* cited by examiner

Primary Examiner—Cary E. O'Connor
(74) Attorney, Agent, or Firm—Womble Carlyle Sandridge & Rice, PLLC; Louis T. Isaf (57) ABSTRACT

An instrument holder including a releasably lockable adjustable arm for rigidly maintaining a tool or instrument in a pre-selected orientation. The instrument holder also includes a tensioning device pivotally connected by a hinge to the arm. The arm includes a plurality of links longitudinally arranged along a common axis, wherein adjacent links are pivotally connected by a hinge, and a duct. A tensioning cable extending within the duct of the arm attaches to the distal end of the articulated arm and to the tensioning device, and applies a tension force to compress the hinges so as to rigidly lock the arm into the preset position.

41 Claims, 4 Drawing Sheets

SURGICAL INSTRUMENT HOLDER

CROSS-REFERENCE TO RELATED APPLICATIONS

This application claims the benefit of provisional application no. 60/252,279, filed Nov. 21, 2000.

FIELD OF THE INVENTION

The present invention relates generally to devices for holding and maintaining a tool or instrument in pre-selected positions. More specifically, the present invention relates to a lockable, adjustable holder for supporting and maintaining a surgical tool or instrument in a desired or selected position.

BACKGROUND

Surgical procedures often require that a tool or instrument be maintained in a pre-selected position and/or apply a constant force to a tissue or organ. The limited area and generally restricted access to most surgical sites on a patient in an operating room or theatre, however, makes it desirable that as few operating theatre personnel as possible surround the patient, thus generally precluding theatre assistants from holding each and every tool. Mechanical holders, therefore, are a preferred choice for holding tools or instruments, offering stability and a compactness that a human assistant cannot provide.

During most surgical procedures, tools or instruments attached to mechanical holders typically have to be constantly adjusted relative to the surgical site, or moved or removed from the surgical site depending on the immediate needs of the operating surgeon. Again, the confined working area demands the minimum number of active persons be present to adjust and reposition the holding devices. There is, therefore, a clear advantage in having tools or instrument holders that can be easily manipulated solely by the surgeon. The workload demands placed upon the surgeon, however, require that the apparatus be operated with a minimum of effort and distraction. Further, since any equipment used in surgery will be in the sterile environment of an operating theatre, mechanical holders also must be able to tolerate sterilization, especially by autoclaving. A simple, sterilizable device that can be adjusted to different positions and be locked into place with a simple operation, demanding little attention from the surgeon is, therefore, highly desirable.

A typical use for an adjustable and releasably lockable instrument holder is in the field of neurosurgery where the brain, or a region thereof, must be retracted or pulled back to allow access to underlying tissue. A blade retractor typically is used in this technique, and may generally be held in position by a surgical assistant. When most conventional brain retractors or holders are held by an assistant, however, there is the potential for shifting or movement of the retractor because of instability of the assistant, or fatigue.

A number of brain retractors and holding apparatus are known in the art. McEwen et al, for example, in U.S. Pat. No. 5,201,325, discloses a pneumatically operating adjustable apparatus comprising several elongated links that are lockable into a pre-selected position. This apparatus requires multiple connections to pressure and pressure sensing apparatus that introduce a complex of wiring to the already crowded surgical environment.

Another conventional lockable instrument holder is the "Greenberg" brain retractor consisting of a plurality of ball and socket joints threaded on a length of cable. When the cable is tightened by a lever mechanism, the friction within each ball and socket is increased and the retraction arm becomes rigid. Limited friction in the ball and socket joints of this device, however, tends to limit the weight of the tool or instrument that can be carried by the retractor. The "Greenberg" retractor further requires that the operator, such as the surgeon, manipulate a mechanical screw means for tightening the cable to lock the retractor in place, which consequently requires a distractive and lengthy drawing of attention away from the surgery.

There is still a need, therefore, for a simple, easily operated surgical tool or instrument holder that will allow a surgeon to position a tool such as a brain retractor and then lock the tool into a substantially fixed, selected position with a minimum of effort.

SUMMARY OF THE INVENTION

Briefly described, the present invention comprises a releasably lockable adjustable instrument holding mechanism for rigidly maintaining a tool or instrument in a pre-selected orientation that will allow a surgeon to position and substantially fix the surgical instrument easily and without extensive or distracting manipulation of a complex locking mechanism. In one aspect of the present invention, the instrument holding mechanism generally comprises an actuatable arm attached to a tensioning cable and a tensioning device having an actuator housing defining an interior cavity and an actuator mechanism such as a conductive wire element. The tensioning cable passes through a duct in the actuator housing communicating with the interior cavity, and the proximal end of the tensioning cable operably connects to at least one electrically conductive wire that is connected to the actuator housing. The tensioning device is pivotally connected to an articulated arm by a hinged joint.

In one aspect of the present invention, the articulated arm includes a plurality of links longitudinally arranged along a common axis, with adjacent links being pivotally connected by a hinged joint. Each link has a lumen or central cavity or duct longitudinally arranged along the common axis so as to define a longitudinally extending passage or duct along the length of the arm. The tensioning cable is slideably disposed within the duct of the arm and through the duct and interior cavity of the actuator housing, and has a distal end attached to the distal end of the articulated arm and a proximal end operably attached to the tensioning device.

In one aspect of the present invention, once the articulated arm has been adjusted to a desired, pre-selected holding position, the tensioning device is engaged, causing an electric current to be passed through the conductive wire, which heats and contracts, thereby applying a tension force to the tensioning cable. This tension force compresses the hinged joints of the articulated arm, so as to rigidly lock the arm into the desired preset position. A switch is provided along with the housing to enable the operator to automatically activate or deactivate the tensioning cable to thus lock or unlock the articulated arm.

In another aspect of the present invention, the instrument holder can further include a frame slideably disposed in the actuator housing of the tensioning device and which is rotatably connected to a tensioning rod having a screw thread thereon. The tensioning device further will typically include an electric motor or similar motorized device and a worm gear or screw, wherein the gear is operably connected to the screw thread of the tensioning rod. The motor is connected to a power source and a switch.

In yet another aspect of the present invention the frame can be slideably disposed in the interior cavity of the actuator housing and will include a threaded hole. The motor of the tensioning device can also include a shaft with a screw thread disposed thereon that operably connects to the threaded hole of the frame.

In addition, the hinged joints of the articulated arm generally will have contacting surfaces having a surface coating such as a bonded tungsten carbide layer thereon. The hinged joints also may have uneven contacting surfaces to increase the strength of the locking action to rigidly maintain the articulated arm in its pre-selected orientation.

It further is contemplated that in all aspects of the present invention, a surgical tool or instrument may be attached to the articulated arm. In particular, the releasably lockable arm of the present invention may be used to rigidly maintain a brain retractor in a desired, selected position, and subsequently released for removal of the retractor from the brain of a patient by the simple operation of a switch. It is within the scope of the present invention, however, that the lockable articulated arm may be connected to a variety of tools or instruments of different sizes and shapes including devices outside the surgical field that are to be maintained at a pre-selected orientation.

Various objects, features, and advantages of the invention will become more apparent upon review of the detailed description set forth below when taken in conjunction with the accompanying drawing figures, which are briefly described as follows.

DETAILED DESCRIPTION

A full and enabling disclosure of the present invention, including the best mode known to the inventor of carrying out the invention is set forth more particularly in the remainder of the specification, including reference to the accompanying drawings, wherein like reference numerals designate corresponding parts throughout several figures. This description is made for the purpose of illustrating the general principles of the invention and should not be taken in the limiting sense.

The present invention is directed to releasably locking a tool or instrument, such as a surgical tool or similar instrument, into a desired or selected position. The present invention is further directed to providing a lockable instrument holder mechanism, which generally comprises a releasably lockable adjustable arm to which a surgical tool may be attached, and which may be orientated and locked rigidly into position by an electrically operable tensioning device.

With reference, therefore, to FIGS. 1–5, the instrument holder mechanism of the present invention generally includes a releasably lockable adjustable arm 100 connected to a tensioning device 120 by hinged joint 104. The arm of the present invention may be, but is not limited to, a single member, or a plurality of links connected by a plurality of hinges, that can pivot relative to a tensioning device, to a patient or to other fixed points of reference and which can be adapted to hold a tool or instrument. The arm also can be any form such as, but not limited to, an elongated member, a spherical member, a helical member, a single member or an articulated member, or any other form that will allow the adjustment of a surgical tool or instrument to a desired pre-selected position. The tensioning device or electrically operable tensioning device, of the present invention imparts a tension force to a tensioning cable 101 when an electric current is applied to the tensioning device 120. The hinge or hinged joint of the present invention can include any adjustable joint mechanism, and typically included a ball and socket type joint. For example, the hinged joint may be a ball and socket joint capable of movement in more than one plane or an elongated convex surface and a receiving concave surface capable of pivoting in one plane. The hinged joint further typically includes a duct or passage through which a cable may pass along the longitudinal axis of the joint. The term "releasably lockable" as used herein refers to rigidly locking an arm or other structure or device in a desired pre-selected orientation relative to a tensioning device, a surgical patient or to any other fixed point of reference, and maintaining the pre-selected position by applying a tension force to a tensioning cable thereby compressing and immobilizing a plurality of hinges. Reduction in the tension force releases the hinges, thereby restoring mobility to the arm.

Figure 1:
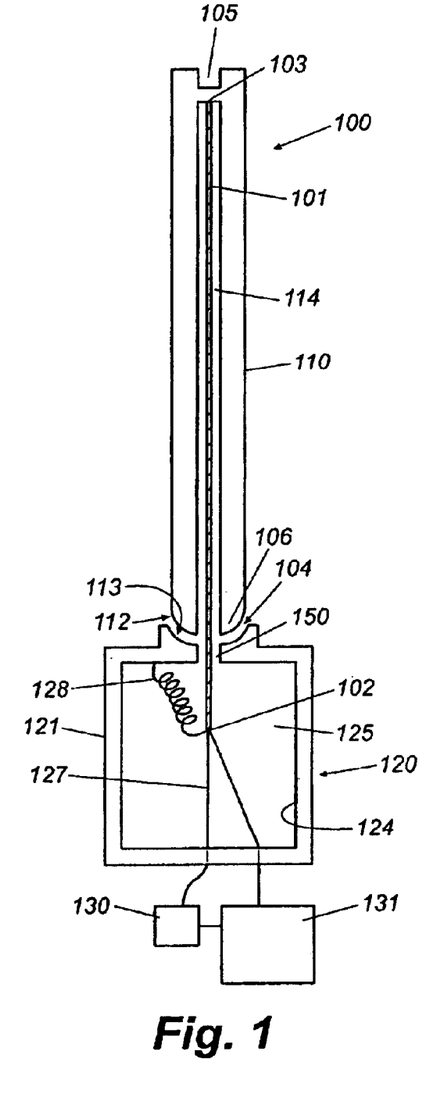
FIG. 1 is a cross-section view illustrating an embodiment of a reversibly lockable adjustable arm made in accordance with the present invention.

In one embodiment of the present invention, illustrated in FIG. 1A, the adjustable arm 100 typically has a longitudinally extending internal passage or duct 114 and a distal end 105 adapted to accept a surgical tool or other instrument. The adjustable arm 100 further has a proximal end 106 connected to the tensioning device 120 by the hinged joint 104. A tensioning cable 101 generally is slideably disposed along the duct 114, the tensioning cable 101 having a proximal end 102 and a distal end 103. The tensioning cable of the present invention can include a flexible cable, wire, string, thread, or filament that will withstand a tension force at least large enough to immobilize a plurality of hinges. The cable can be constructed of any material with sufficient tensile strength to allow a tension to be applied to the arm without the cable breaking such as, but not limited to, a metallic wire, a metallic alloy, or natural or synthetic polymer or monomer. The distal end 103 of the tensioning cable 101 is attached to the distal end 105 of the adjustable arm 100, and the proximal end 102 of the cable 101 is attached to the tensioning device 120.

It is to be understood that the present invention contemplates that the tensioning cable 101 may be of any length, and attached to the adjustable arm 100 at any point that allows the adjustable arm 100 to pivot about the hinge 104 and which will allow a tension force in the tensioning cable 101 to compress the hinge 104.

Figure 2:
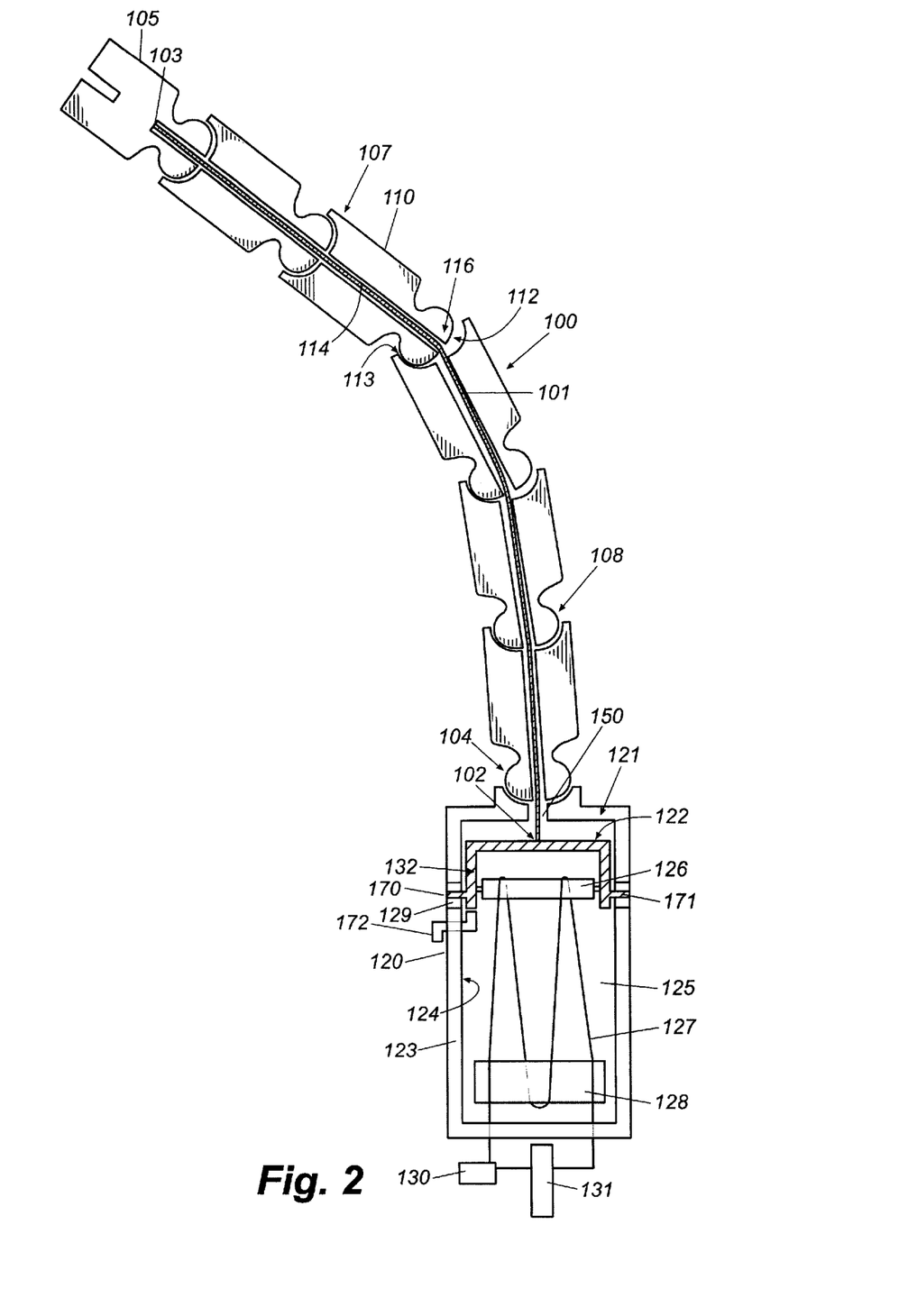
FIG. 2 is a cross-sectional view illustrating another embodiment of a reversibly lockable adjustable arm of the present invention.

In another embodiment of the present invention, as shown in FIG. 2A, the releasably lockable adjustable arm 100 can be included in a series of adjacent links 110 disposed along a longitudinal axis and interconnected by a plurality of hinged joints 104 to enable the arm to be articulated into various desired positions and/or configurations.

One embodiment of the electrically operable tensioning device 120 of the present invention includes an actuator housing 121, an interior cavity 125 defined by an interior wall 124 and a duct or passage 150 traversing the interior wall 124 and communicating with the interior cavity 125. The actuator housing 121 of the present invention is understood to be any body comprising a wall defining an interior cavity that may be used to contain the tension generating mechanism of the tensioning device. The interior cavity of the "actuator housing" also may be sealed from the exterior so that steam or sterilizing gases cannot penetrate into the interior cavity. If not sealed, the actuator housing may contain at least one drain duct to allow condensation to escape from the housing. The tensioning cable 101 that is disposed in the duct 114 of the adjustable arm 100 further passes through the duct 150. The proximal end 102 of the tensioning cable 101 typically being attached to an actuator mechanism 126, such as an electrically conductive wire 127.

The electrically conductive wire 127 of the tensioning device is electrically connected to a switch 130 and a power source 131, and to the housing 121. The switch 130 will break an electric circuit and may be, but is not limited to, a single polarity switch, a reversible polarity switch, a hand operated switch, a foot switch, a voice activated switch, a computer regulated switch, or any other similar device known to one of ordinary skill in the art and which can close or open an electric circuit or otherwise disengage the tension generating mechanism. The electrically conductive wire 127, is supplied with electrical power from the power source 131 by the operation of the switch 130, causing the wire to be heated and to contract so as to apply a tension force to the tensioning cable 101. The tension force is maintained while the electrically conductive wire is heated. This tension force in the tensioning cable 101 locks the hinged joint(s) 104 in a fixed position by compressing the hinged joint(s) 104, thereby increasing the friction within the hinged joints 104, so as to rigidly maintaining the adjustable arm 100 in a desired pre-selected position.

While not wishing to limit the scope of the present invention, the electrically conductive wire 127 of the present invention generally can include a shape memory alloy having a "two-way" shape memory such that when the wire 127 is heated by an electric current the alloy contracts and when cooled the alloy returns to its original length when a tension force is applied thereto, as described in Liu & McCormick, Acta Metallurgica, 38, 1321–1326 (1190); Nishida & Monma, Scripta Metallurgiea, 18, 1293–1298 (1984); Duerig & Melton, MRS International Meeting on Advanced Materials, 9, 581–597 (1989) and incorporated herein by reference in their entireties. The alloy may be, but is not limited to, a titanium-nickel alloy such as FLEXI-NOL™ (Dyna Alloy, Inc.) or FLEXTUBE™ microtubing. The electrically conductive wire 127 further may be formed with any desired shape of shape memory alloy such as, but not limited to, a cylindrical wire, a ribbon, strip, or a sheet that will allow the passage of an electric current to heat the alloy and cause the wire 127 to contract.

A tensioning mechanism 128 such as, for example, a spring connecting the wire 127 to the housing 121 may apply a tensioning force to the wire 127. When the electric current is discontinued, the wire 127 will cool and the tensioning force from the tensioning mechanism 128 will tend to cause the wire 127 to lengthen or expand. This expansion or elongation of the wire 127 will release the locking force applied to the hinged joint(s) 104. It is contemplated to be within the scope of the present invention for the tensioning mechanism 128 to be, for example, a spring, a lever, a rotatable cam, a contractable or an extendable arm configured to apply a tension force to the wire 127. The tension force may be constantly applied to the wire 127 with a constant or variable intensity, or only applied when, for example, it is desirable to release the locked hinged joint(s) 104.

In another embodiment of the present invention, the tensioning device 120 includes a slideable frame 122 disposed in the interior cavity 125 of the actuator housing 121 and connected to the proximal end 102 of the tensioning cable 101. The frame 122 is a device that may slideably move relative to the actuator housing, and to which a tensioning cable is attached. The frame is further attached to a mechanism to apply a pulling force to the tensioning cable. The slideable frame 122 is further connected to at least one electrically conductive wire 127, wherein at least one end of the electrically conductive wire 127 is attached to the actuator housing 121 of the tensioning device 120. The electrically conductive wire 127 is electrically connected to a switch 130 and a power source 131. When the electrically conductive wire 127 is connected to an electric current, the wire 127 heats and contracts and pulls the slideable frame 122 relative to the adjustable arm 100 so as to apply a tension force to the attached tensioning cable 101.

The present invention further contemplates that the slideable frame 122 of the tensioning device 120 may be movable relative to the tensioning cable 101 by the operation of a screw 141 and a motor 140.

Figure 1B:
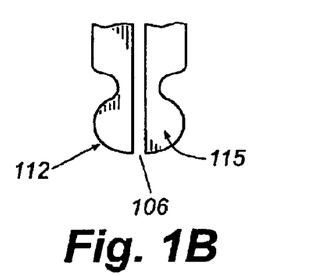
FIG. 1B illustrates one embodiment of the hinged joint of the arm of the present invention, wherein the hinged joint is a ball and socket joint.
Figure 1C:
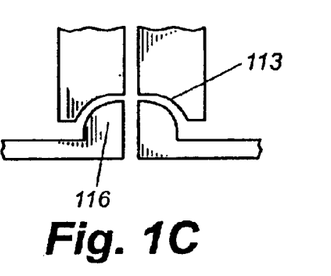
FIG. 1C illustrates another embodiment of a ball and socket connection for the hinge joint of the arm.
Figure 1D:
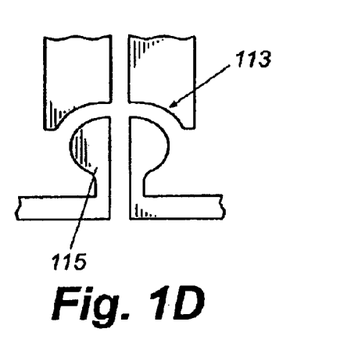
FIG. 1D illustrates still another embodiment of a ball and socket connection for the hinge joint of the arm.

Various example embodiments of the hinged joints 104 for connecting the adjustable arm 100 to the tensioning device 120, as contemplated by the present invention, are illustrated in FIGS. 1A–1E. It is to be understood, however, that the embodiments of the hinged joints 104 as illustrated in FIGS. 1A–1E are examples only and should not be construed as limiting the form of any hinged joint 104 of the present invention. In a first embodiment of the hinged joint 104 shown in FIG. 1A, the hinged joint 104 includes a ball and socket joint to enable movement in several directions or planes, and wherein the proximal end 106 of the adjustable arm 100 has a convex surface 112. In another embodiment, as shown in FIG. 1B, the proximal end 106 of the adjustable arm 100 is a stud 115 with a convex surface 112. In other embodiments, the proximal end 106 of the adjustable arm 100 has a concave cavity 113, as shown in FIGS. 1C and 1D. The embodiments of the hinge 104 shown in FIGS. 1A and 1B include a concave cavity 113 formed along the tensioning device 120, wherein concave cavity 113 receives the convex surface 112 of the proximal end 106 of the adjustable arm 100. In the ball and socket joint embodiments of the hinged joint 104 shown in FIGS. 1C and 1D, the convex surface 112 is provided on a protuberance 116 or a stud 115 on the tensioning device 120, and the convex surface 112 is received by the concave cavity 113 at the proximal end 106 of the adjustable arm 100.

Figure 1E:
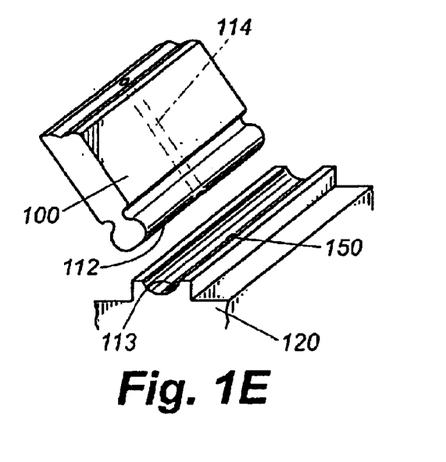
FIG. 1E illustrates still another embodiment of the hinged joint of the present invention.

In a further embodiment of the hinged joint 104 illustrated in FIG. 1E, the joint is formed as an elongated hinge designed to rotate in primarily one plane, wherein the elongated curved surface 112 is received by the elongated concave cavity 113.

While not wishing to limit in any way the scope of the present invention, the contacting surfaces of the convex surface 112 and the concave cavity 113 of the hinged joints 104 further typically are not polished and generally have a coating such as a bonded tungsten carbide. The present invention, however, contemplates that any material, coating and/or surface texture may be used that allows the hinge 104 to be locked and immobilized by a compressive force in a desired position and being able to resist movement when a load such as the weight of a tool or instrument, or a tissue retraction force is applied to the distal end 105 of the adjustable arm 100.

To operate the instrument holder of the present invention as illustrated in FIGS. 1A–1E, the adjustable arm 100 generally is pivoted about its hinged joint 104 to a desired pre-selected position. The switch 130 is then closed to pass an electric current from the power source 131 through the electrically conductive wire 127, whereupon the electrically conductive wire 127 heats and contracts, pulling the tensioning cable 101 relative to the adjustable arm 100. The tension force generated by the pulling of the tensioning cable compresses the hinged joint 104, and increases the friction between the convex surface 112 and the receiving concave cavity 113 of the hinged joint 104, so as to rigidly lock the hinged joint 104. The adjustable arm 100 is, therefore, maintained in its pre-selected position relative to the tensioning device 120 for as long as the current heats the wire 127. When the switch is in the open or off position, the electric current no longer passes through the electrically conductive wire 127, which then cools and expands to about its original, pre-heated length when a tension force is applied thereto, thus releasing the tension force applied to the tensioning cable 101, so as to release the adjustable arm 100 from its locked position.

In another embodiment of the present invention, as shown in FIG. 2, the adjustable arm 100 is an articulated adjustable arm 100 having a plurality of links 110 arranged along a longitudinal axis and interconnected by a plurality of hinged joints 104. In this embodiment, shown in FIG. 2, the number of links 110 and the interconnecting hinged joints 104 are not limited in length or number and generally are selected so as to allow the adjustable arm 100 to be positioned in a desired and pre-selected orientation. The embodiment shown in FIG. 2, therefore, should not be considered limiting in this regard.

Each link 110 of the plurality of links has a longitudinal duct or lumen 114, a distal end 107, and a proximal end 108, wherein the distal end 107 of each link has a concave cavity 113, and the proximal end 108 has a convex protuberance 116, and wherein the convex surface 112 of each convex protuberance 116 is received by the concave cavity 113 of an adjacent link 110, to form a plurality of hinges 104 connecting the plurality of links 110 along the common longitudinal axis. As shown in FIG. 2, the hinged joints 104 are ball and socket joints capable of movement about a plurality of planes. It is within the scope of the present invention, however, that the plurality of hinged joints 104 may be elongated hinges, ball and socket hinges, or any combination thereof. When the plurality of links 110 are interconnected by the plurality of hinged joints 104, the ducts 114 of the adjacent links 110 have a common axis, and therefore form a continuous duct or passage 114 connecting the distal end 107 and the proximal end 108 of the adjustable arm 100.

As shown in FIG. 2, the duct 114 further will have a tensioning cable 101 slideably disposed therein, the tensioning cable 101 having a distal end 103 and a proximal end 102. The distal end 103 of the tensioning cable 101 is attached to the distal end 105 of the adjustable arm 101. The tensioning cable 101 is further slideably disposed through a duct 150 in the hinge 104 attached to the actuator housing 121, so as to allow the proximal end 102 of the tensioning cable 101 to pass through the interior cavity 125 of the actuator housing 121.

As further shown in FIG. 2, the proximal end 102 of the tensioning cable 101 is attached to a frame 122 slideably disposed in the interior cavity of the actuator housing 121. The frame 122 generally includes a member 124 having a first rod 126 with a longitudinal axis. A second rod 128 with a longitudinal axis is attached to the actuator housing 121. It is contemplated that the first rod 126 and the second rod 128 may be rotatable about the longitudinal axes thereof, or immobile or a combination thereof. The rods 126 and 128 may be of any material including, but not limited to, plastic or metal. In one embodiment, the rods 126 and 128 are formed from an electrically non-conductive plastic that will not totally resist movement of the electrically conductive wire 127 disposed thereon. At least one electrically conductive wire 127 is slideably looped around the first rod 126 and the second rod 128, with the ends of the wire 127 attached to the actuator housing 121 and electrically connected to a power source 131 and a switch 130. In yet another embodiment of the tensioning device 120 of the present invention, the electrically conductive wire 127 can be looped around only the first rod 126.

As is also illustrated in FIG. 2, a movement-limiting device 170, including at least one peg 171, is attached to the frame 122, with the peg 171 is slideably disposed in a cavity 129 in the actuator housing 121. A movement-limiting device as understood by the present invention is a device that will restrict the pulling of a tensioning cable and thereby place an upper limit on the tension force exerted on the tensioning cable. The movement-limiting device 171 includes, but is not limited to, a pre-selected length of an electrically conductive cable, a movement-limiting peg, a peg and cavity device, a collar attached to the tensioning cable, a tension measuring device connected to a switch, or any other device that will restrict the force being applied to the tensioning cable. Other embodiments of the movement-limiting device 170, are also contemplated by the present invention. In one such embodiment, the peg 171 is attached to the wall 123 defining the interior cavity 125 of the actuator housing 121, and the peg 171 is slideably disposed in a cavity 129 in the frame 122 disposed in the interior cavity 125.

Further illustrated in FIG. 2 is an optional rotatable cam 172 that may be rotated to engage the frame 122, thereby applying a tension force to the wire 127. The tension force will increase the length of the wire 127 when the electric current applied thereto.

Figure 3A:
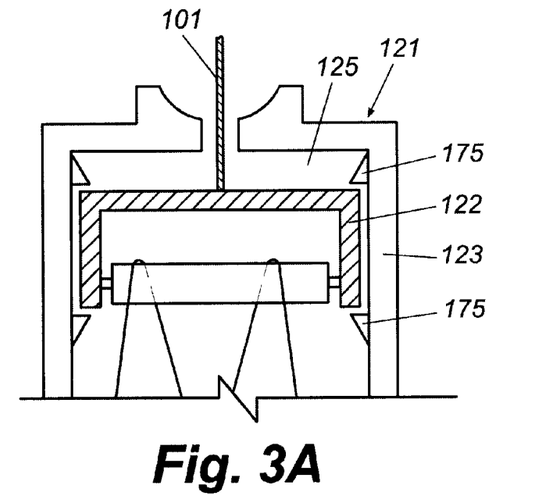
FIG. 3A is a cross-sectional view illustrating an embodiment of a movement-limiting device for the arm of the present invention.
Figure 3B:
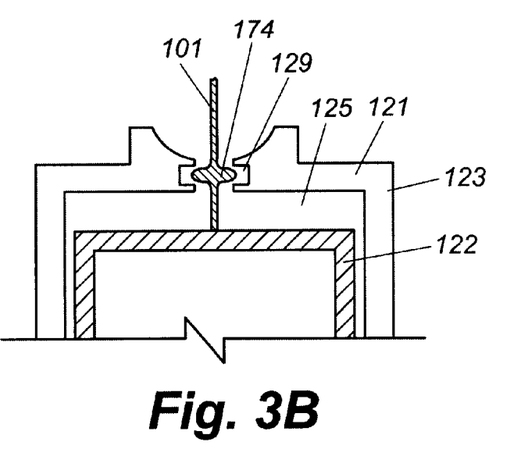
FIG. 3B is a cross-sectional view illustrating another embodiment of the movement-limiting device of the present invention.
Figure 3C:
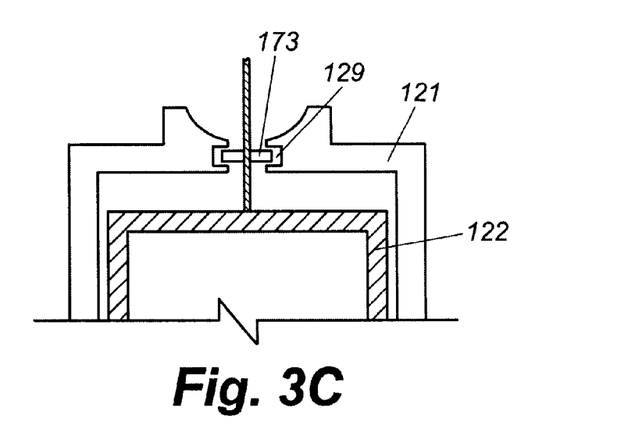
FIG. 3C is a cross-sectional view illustrating yet another embodiment of the movement-limiting device of the present invention.

The present invention further contemplates, but is not limited to, other embodiments of the movement-limiting device 170, such as the examples illustrated in FIGS. 3A–3C. In one embodiment shown in FIG. 3A, the movement-limiting device has at least one peg 171 attached to the wall 123 defining the interior cavity 125 of the actuator housing 121 and protruding into the interior cavity 125 so as to limit movement of the frame 122. In another embodiment of the present invention, as illustrated in FIG. 3B, the movement-limiting device 170 has at least one protuberance 172 formed in or mounted along the tensioning cable 101 and slideably disposed in a cavity 129 of the actuator housing 121. In yet another embodiment of the present invention, the movement-limiting device 170 includes a collar 173 attached to the tensioning cable 101, wherein the collar 173 is slideably disposed in the cavity 129 of the activator housing 121.

Still another embodiment of the movement-limiting device 170 of the present invention is an electrically operable tension sensitive device electrically connected to the switch 130. The tension sensitive device detects when the tension force in the tensioning cable has reached a desired pre-selected value, whereupon the switch 130 is opened by the tension sensitive device.

In operation of the embodiment of the present invention shown in FIG. 2, the articulated adjustable arm 100 is arranged in a desired pre-selected orientation, after which switch 130 is closed to enable power from the power source 131 to be supplied to the electrically conductive wire 127, heating the wire and causing it to contract. The contraction of the wire 127 pulls the first rod 126 toward the second rod 128, reducing the distance between the rods 126 and 128 and thereby pulling the frame 122 and the tensioning cable 101 attached thereto relative to the adjustable arm 100. This generates a tension force in the tensioning cable 101. The tension cable accordingly pulls the distal end 105 of the adjustable arm 100 towards the proximal end 106 of the adjustable arm 100 which in turn compresses and immobilizes the plurality of hinged joints 104, locking the adjustable arm 100 in the desired pre-selected orientation. When the adjustable arm 100 must be arranged to a different orientation, the switch 130 is opened, shutting off power to the electrically conductive wire 127, which cools. A tension force is applied to the cooled shaped metal alloy wire 127 by a tensioning means 128, such as a spring or a rotatable cam 172, thereby increasing the length of the cooled wire 127 so as to release the tension force in the tensioning cable 101. The compressive pressure applied to the plurality of hinged joints 104 is reduced, and mobility of the hinged joints 104 is restored. The plurality of links 110 of the articulated adjustable arm 100 can then be repositioned.

Figures 4, 5:
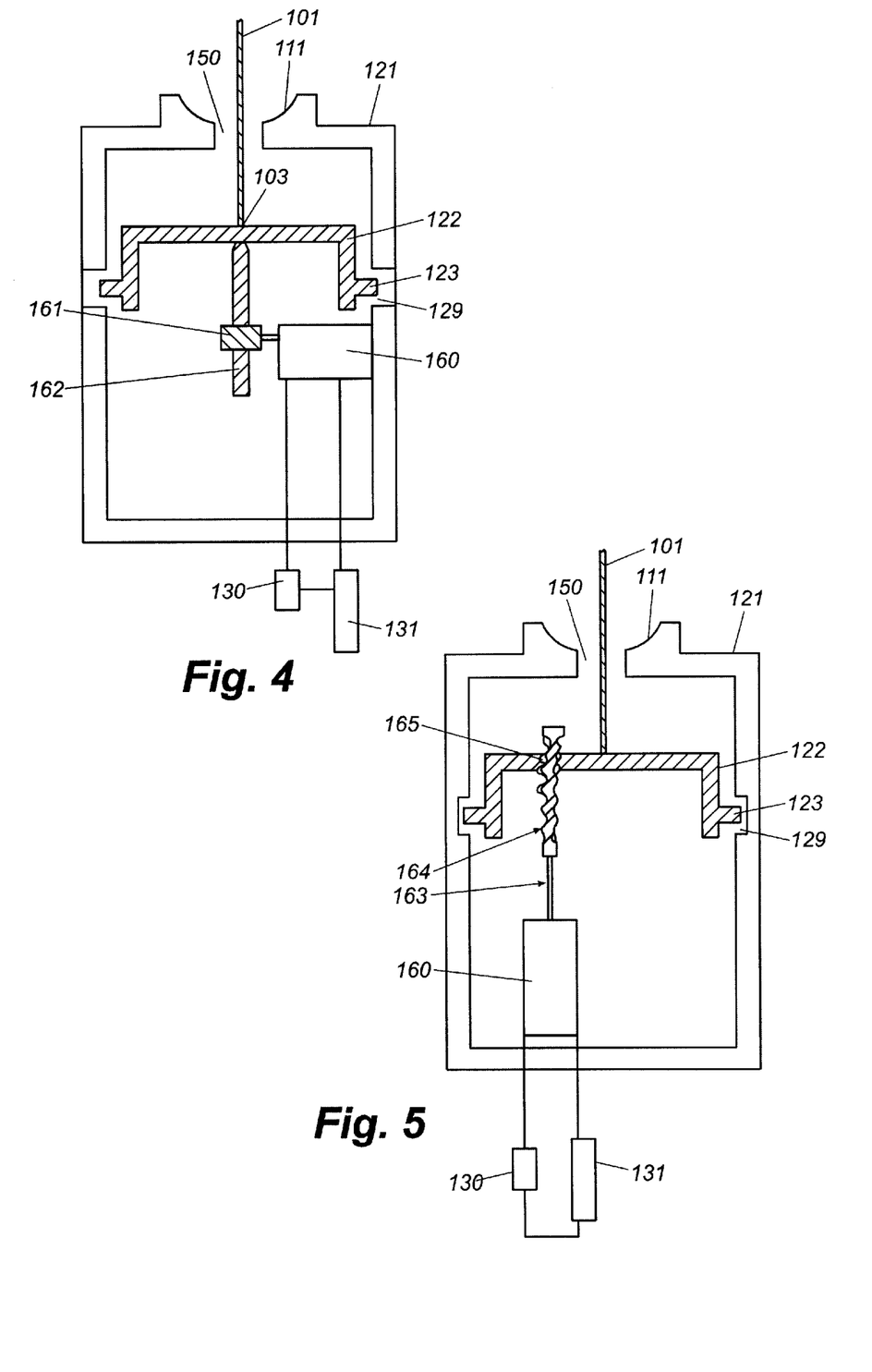
FIG. 4 is a cross-sectional view illustrating an embodiment of the tensioning device for the present invention.
FIG. 5 is a cross-sectional view illustrating another embodiment of the tensioning device for the present invention.

The present invention further contemplates that the embodiments of the adjustable arm 100, as illustrated in FIGS. 1A–2, may be connected to other embodiments of the tensioning device 120 besides those shown in FIGS. 1A–2. For example, another embodiment of the tensioning device 120 of the present invention that may be connected to the adjustable arm 100 by a hinged joint 104 is illustrated in FIG. 4, wherein the tensioning device 120 includes a motor 160 having a worm gear 161 thereon, operably engaged with a threaded tensioning rod 162. The threaded tensioning rod 162 is rotatably engaged with a frame 122 that is slideably disposed in an actuator housing 121 and to which is attached the proximal end 103 of the tensioning cable 101 of the adjustable arm 100. The motor 160 is electrically connected to a reversible switch 130 and a power source 131.

When the switch 130 is closed, the motor 160 rotates the worm gear 162 operably engaged with the tension rod 162, and lowers the tension rod 162 and the frame 122 attached thereto, so as to pull the tensioning cable 101 attached to the frame 122. When the switch 130 is moved to its off position, rotation of the worm gear 162 stops so as to maintain a constant tension force in the tensioning cable 101. When the switch 130 reverses, the motor 160 and the worm gear 162 expand or urge the frame 122, thereby releasing the tension force in the tensioning cable 101 so as to relieve the compression of the plurality of the hinges 104 of the adjustable arm 100.

In yet another embodiment of the tensioning device 120 of the present invention as illustrated in FIG. 5, the motor 160 has a shaft 163 with a thread 164 disposed thereon, operably engaged with a threaded duct 165 in a frame 122 slideably disposed in an actuator housing 121 of the tensioning device 120. The tensioning device 120 may further comprise a movement-limiting device 170 as illustrated, for example, in FIGS. 3A–3D. A motor 160 is connected to a switch 130 and a power source 131. Closing the switch 130 activates the motor 160 and rotates the shaft 163 so as to pull the frame 122 towards the motor 160. This applies a tension force to the tensioning cable 101 attached to the frame 122. The motor 130 is stopped to maintain the tension force in the tensioning cable 101. When the switch 130 is reversed to reverse the motion of the motor 160, the tension force is released. The compression of the plurality of the hinged joints 104 of the adjustable arm 100 is thereby relieved and mobility of the adjustable arm 100 is restored.

The present invention thus addresses the need of a surgeon to rigidly maintain a surgical tool in position in the patient by a simple operation that demands minimum attention and manipulation on the part of the surgeon. The present invention further addresses the need for the locking device for the instrument holder to be easily operable by the surgeon using a simple switch, without requiring additional personnel in a crowded surgical theatre.

Although the illustrated aspects and embodiments of the instrument holder of the present invention are intended to provide a releasably lockable adjustable arm for rigidly maintaining a brain retractor in a desired pre-selected orientation, the present invention also contemplates that other surgical tools and instruments may be attached to the instrument holder. The present invention contemplates further that the releasably lockable and adjustable arm may also be used in any field other than in surgery that requires a releasably lockable arm that can hold a tool or instrument in a desired pre-selected position and that may be activated by the operation of a simple switch. It should also be understood that any embodiments of the releasably lockable adjustable arm of the present invention can be stably supported by attachment to a support device. A support device of the present invention is an apparatus, device or mechanism to which the instrument holder of the present invention can be attached so that it is not necessary for the instrument holder to be supported by a human. The present invention contemplates that a support device can be, but is not limited to, a pole, a floor stand, or a surgical operating table or frame attached thereto.

With respect to the above description, it is to be realized that the optimum dimensional relationships for the parts of the invention, to include variations in size, materials, shape, form, function and manner of operation, assembly, and use, are deemed readily apparent and obvious to one skilled in the art, and all equivalent relationships to those illustrated in the drawing and described in the specification are intended to be encompassed by the present invention. Further, the various components of the embodiments of the invention may be interchanged to produce further embodiments and these further embodiments are intended to be encompassed by the present invention.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. An instrument holder for rigidly maintaining an instrument in a pre-selected orientation, comprising:

a tensioning device;

an arm having a distal end, a proximal end, and a longitudinally arranged duct, wherein the arm is pivotally connected by a joint to the tensioning device; and a tensioning cable slideably disposed within the duct of the arm and having a distal end attached to the distal end of the arm and a proximal end operably attached to the tensioning device; and wherein the tensioning device comprises an actuator housing having an interior wall defining an interior cavity and a duct communicating with the interior cavity, wherein the tensioning cable is slideably disposed through the duct of the actuator housing; and at least one electrically conductive wire operably connecting the proximal end of the tensioning cable to the actuator housing, and wherein the electrically conductive wire is connected to a power source and a switch.

2. The instrument holder of claim 1, wherein the distal end of the arm is adapted to accept a tool or instrument.

3. The instrument holder of claim 1, wherein the arm is attached to a support device.

4. The instrument holder of claim 1, wherein the joint comprises a ball and socket joint or an elongated hinge.

5. The instrument holder of claim 1, wherein the joint comprises unpolished contacting surfaces.

6. The instrument holder of claim 1, wherein the tensioning device is connected to a switch and to a power source selected from a fixed electricity supply, a battery, a rechargeable battery and a photovoltaic cell.

7. The instrument holder of claim 1, wherein the arm comprises a plurality of links longitudinally arranged along a common axis, wherein adjacent links are pivotally connected by a hinged joint, and each link has a duct longitudinally arranged with a common axis.

8. The instrument holder of claim 7, wherein the hinged joints linking adjacent links are ball and socket joints, elongated hinges or a combination thereof.

9. The instrument holder of claim 7, wherein the hinged joints included unpolished contacting surfaces.

10. The instrument holder of claim 7, wherein each link of the plurality of links further comprises:

a distal end having a concave cavity; and a proximal end having a convex surface, wherein the convex surface of each link is received by the concave cavity of an adjacent link, thereby forming a hinged joint.

11. The instrument holder of claim 7, wherein each link of the plurality of links further comprises:

a distal end having a convex surface; and a proximal end having a concave cavity, the concave cavity of each link receiving the convex surface of an adjacent link, thereby forming a hinged joint.

12. The instrument holder of claim 1, further comprising a frame slideably disposed in the interior cavity of the actuator housing and connected to the proximal end of the tensioning cable and the electrically conductive wire.

13. The instrument holder of 12, wherein the frame further comprises a first rod having the electrically conductive wire disposed thereon and a second rod, and wherein the wire has a first end and a second end attached to the actuator housing.

14. The instrument holder of claim 13, further comprising a second rod attached to the actuator housing, wherein the electrically conductive wire is looped around the first and second rods, and wherein the wire has a first end and a second end attached to the actuator housing.

15. The instrument holder of claim 1, further comprising a movement limiting device.

16. The instrument holder of claim 1, wherein the electrically conductive wire contracts when connected to an electric power source.

17. The instrument holder of claim 1, wherein the electrically conductive wire comprises a shape memory alloy.

18. The instrument holder of claim 17, further comprising a tensioning mechanism for applying a tension force to the electrically conductive wire.

19. The instrument holder of claim 17, wherein the electrically conductive wire comprises a tungsten-nickel alloy.

20. The instrument holder of claim 1, wherein the electric power source comprises a battery, a rechargeable battery, a fixed electrical supply or a photovoltaic cell.

21. The instrument holder of claim 1, wherein the electric switch is selected from the group consisting of a reversible polarity switch, a hand-operable switch, a foot-operable switch, a voice-activated switch, an electronically regulated switch and a computer-regulated switch.

22. The instrument holder of claim 1, further comprising a surgical device connected to the distal end of the arm.

23. The instrument holder of claim 22, wherein the surgical device comprises a brain retractor.

24. The instrument holder of claim 1, wherein the joint includes contacting surfaces comprised of tungsten carbide.

25. An instrument holder for rigidly maintaining an instrument in a pre-selected orientation, comprising:

a tensioning device;

an arm having a distal end, a proximal end, and a longitudinally arranged duct, wherein the arm is pivotally connected by a joint to the tensioning device; and a tensioning cable slideably disposed within the duct of the arm and having a distal end attached to the distal end of the arm and a proximal end operably attached to the tensioning device; and wherein the tensioning device comprises an actuator housing having an interior wall defining an interior cavity and a duct communicating with the interior cavity, wherein the tensioning cable is slideably disposed through the duct of the actuator housing;

a frame slideably disposed in the interior cavity of the actuator housing and attached to the proximal end of the tensioning cable; and a tensioning rod having a thread thereon and rotatably connected to the frame; and a motor having a worm gear, wherein the worm gear is operably engaged with the thread of the tensioning rod.

26. The instrument holder of claim 25, the joint includes contacting surfaces comprised of tungsten carbide.

27. An instrument holder for rigidly maintaining an instrument in a pre-selected orientation, comprising:

a tensioning device;

an arm having a distal end, a proximal end, and a longitudinally arranged duct, wherein the arm is pivotally connected by a joint to the tensioning device; and a tensioning cable slideably disposed within the duct of the arm and having a distal end attached to the distal end of the arm and a proximal end operably attached to the tensioning device; and wherein the tensioning device comprises an actuator housing having an interior wall defining an interior cavity and a duct communicating with the interior cavity, wherein the tensioning cable is slideably disposed through the duct of the actuator housing;

a frame slideably disposed in the interior cavity of the actuator housing and attached to the proximal end of the tensioning cable; and a motor having a shaft operably engaged with the frame, wherein the motor is connected to a power source and a reversible polarity switch.

28. The instrument holder of claim 27, the joint includes contacting surfaces comprised of tungsten carbide.

29. An instrument holder for rigidly maintaining an instrument in a pre-selected orientation, comprising:

a tensioning device;

an arm having a distal end, a proximal end, and a longitudinally arranged duct, wherein the arm is pivotally connected by a joint to the tensioning device;

a tensioning cable slideably disposed within the duct of the arm and having a distal end attached to the distal end of the arm and a proximal end operably attached to the tensioning device; and a movement limiting device comprising
at least one peg; and
at least one cavity, wherein the peg is slideably disposed within the cavity.

30. The instrument holder of claim 29, the joint includes contacting surfaces comprised of tungsten carbide.

31. An instrument holder for rigidly maintaining an instrument in a pre-selected orientation, comprising:

a tensioning device;

an arm having a distal end, a proximal end, and a longitudinally arranged duct, wherein the arm is pivotally connected by a joint to the tensioning device;

a tensioning cable slideably disposed within the duct of the arm and having a distal end attached to the distal end of the arm and a proximal end operably attached to the tensioning device; and a movement limiting device;

wherein the tensioning device includes an actuator housing having an interior wall defining an interior cavity and a duct communicating with the interior cavity, wherein the tensioning cable is slideably disposed through the duct of the actuator housing; and wherein the movement limiting device comprises at least one peg projecting from the actuator housing into the interior cavity of the actuator housing.

32. The instrument holder of claim 31, wherein the joint includes contacting surfaces comprised of tungsten carbide.

33. An instrument holder for rigidly maintaining an instrument in a pre-selected orientation, comprising:

a tensioning device;

an arm having a distal end, a proximal end, and a longitudinally arranged duct, wherein the arm is pivotally connected by a joint to the tensioning device;

a tensioning cable slideably disposed within the duct of the arm and having a distal end attached to the distal end of the arm and a proximal end operably attached to the tensioning device; and a movement limiting device;

wherein the tensioning device includes
an actuator housing having an interior wall defining an interior cavity and a duct communicating with the interior cavity, wherein the tensioning cable is slideably disposed through the duct of the actuator housing; and
a frame slideably disposed in the interior cavity of the actuator housing and attached to the proximal end of the tensioning cable; and wherein the movement limiting device is selected from (a) at least one peg attached to the frame and which is slideably disposed in at least one cavity in the wall of the actuator housing and (b) at least one peg attached to the wall of the actuator housing and which is slideably disposed in at least one cavity in the frame.

34. The instrument holder of claim 33, wherein the joint includes contacting surfaces comprised of tungsten carbide.

35. An instrument holder for rigidly maintaining an instrument in a pre-selected orientation, comprising:

a tensioning device;

an arm having a distal end, a proximal end, and a longitudinally arranged duct, wherein the arm is pivotally connected by a joint to the tensioning device;

a tensioning cable slideably disposed within the duct of the arm and having a distal end attached to the distal end of the arm and a proximal end operably attached to the tensioning device; and a movement limiting device including a tension-sensitive switch.

36. The instrument holder of claim 35, wherein the joint includes contacting surfaces comprised of tungsten carbide.

37. An instrument holder for rigidly maintaining an instrument in a pre-selected orientation, comprising:

a tensioning device;

an arm having a distal end, a proximal end, and a longitudinally arranged duct, wherein the arm is pivotally connected by a joint to the tensioning device;

a tensioning cable slideably disposed within the duct of the arm and having a distal end attached to the distal end of the arm and a proximal end operably attached to the tensioning device; and a movement limiting device comprising at least one protuberance along the cable or a collar attached to the cable;

wherein the tensioning device includes an actuator housing having an interior wall defining an interior cavity and a duct communicating with the interior cavity, wherein the tensioning cable is slideably disposed through the duct of the actuator housing; and wherein the protuberance or collar are slideably disposed in a cavity in the wall of the actuator housing.

38. The instrument holder of claim 35, wherein the joint includes contacting surfaces comprised of tungsten carbide.

39. A method of releasably positioning an adjustable arm for rigidly maintaining a pre-selected orientation, comprising the steps:

(a) adjusting the adjustable arm to a pre-selected orientation;

(b) activating a tensioning device to apply a tension force to a tensioning cable attached to the adjustable arm (c) compressing at least one hinge of the arm to secure the arm in the pre-selected orientation; and (d) releasing the tension force applied to the tensioning cable to enable the adjustable arm to be repositioned wherein step (b) further comprises the steps of
(i) applying an electric current to an electrically conductive wire; and
(ii) contracting the electrically conductive wire to apply a tension force to the tensioning cable; and wherein step (d) further comprises the steps of
(i) interrupting the electric current to the electrically conductive wire; and
(ii) allowing the electrically conductive wire to expand to release the tension force applied to the tensioning cable.

40. The method of claim 39, wherein step (d)(ii) further comprises the step of applying tension to e electrically conductive wire.

41. A method of releasably positioning an adjustable arm for rigidly maintaining a pre-selected orientation, comprising the steps:
- (a) adjusting the adjustable arm to a pre-selected orientation;
- (b) activating a tensioning device to apply a tension force to a tensioning cable attached to the adjustable arm;
- (c) compressing at least one hinge of the arm to secure the arm in the pre-selected orientation; and
- (d) releasing the tension force applied to the tensioning cable to enable the adjustable arm to be repositioned;

wherein step (b) further comprises the steps of
- (i) operating a motor to retract a slideable frame having a tensioning cable attached thereto;
- (ii) applying a tension force to the tensioning cable; and
- (iii) disengaging the motor and maintaining the tension force applied to the tensioning cable, and wherein step (d) further comprises the step of reversing the operation of the motor, thereby releasing the tension in the tensioning cable.

* * * * *